(12) United States Patent
Levis

(10) Patent No.: US 11,315,691 B2
(45) Date of Patent: Apr. 26, 2022

(54) METHOD FOR RECOMMENDING CONTINUING EDUCATION TO HEALTH PROFESSIONALS BASED ON PATIENT OUTCOMES

(71) Applicant: IMPACTIVO, LLC, San Juan, PR (US)

(72) Inventor: Maria Levis, San Juan, PR (US)

(73) Assignee: IMPACTIVO, LLC, San Juan, PR (US)

( * ) Notice: Subject to any disclaimer, the term of this patent is extended or adjusted under 35 U.S.C. 154(b) by 60 days.

(21) Appl. No.: 16/282,910

(22) Filed: Feb. 22, 2019

(65) Prior Publication Data
US 2020/0273585 A1 Aug. 27, 2020

(51) Int. Cl.
| | |
|---|---|
| *G16H 70/20* | (2018.01) |
| *G16H 80/00* | (2018.01) |
| *G06Q 10/10* | (2012.01) |
| *G16H 40/20* | (2018.01) |
| *G16H 10/60* | (2018.01) |
| *G16H 50/20* | (2018.01) |

(52) U.S. Cl.
CPC ............ *G16H 70/20* (2018.01); *G06Q 10/10* (2013.01); *G16H 80/00* (2018.01); *G16H 10/60* (2018.01); *G16H 40/20* (2018.01); *G16H 50/20* (2018.01)

(58) Field of Classification Search
CPC .. G06Q 50/22–24; G06Q 10/10; G16H 10/60; G16H 40/20; G16H 50/20; G16H 70/20; G16H 80/00; G06F 19/30; G06F 19/32; G06F 19/325; G06F 19/328; G06F 19/34

USPC .......................................................... 705/2
See application file for complete search history.

(56) References Cited

U.S. PATENT DOCUMENTS

| | | | |
|---|---|---|---|
| 10,540,448 B2* | 1/2020 | Anand | G16H 50/20 |
| 11,132,749 B1* | 9/2021 | Konson | G06F 3/04817 |
| 2002/0127525 A1* | 9/2002 | Arington | G09B 7/04 434/262 |

(Continued)

FOREIGN PATENT DOCUMENTS

EP 3686897 A1 * 7/2020 ............. G16H 10/60

OTHER PUBLICATIONS

Kiamlaluno, Fago, Apr. 19, 2009, "Implementing configurable actions/conditions", Drupal, all pages, http://web.archive.org/web/20160425224214/https://www.drupal.org/node/298534 (Year: 2009).*

(Continued)

*Primary Examiner* — Jason S Tiedeman
*Assistant Examiner* — Jessica Marie Webb
(74) *Attorney, Agent, or Firm* — Innovation Capital Law Group, LLP; Vic Lin

(57) ABSTRACT

Methods and systems for providing health professionals with continued education are based on performance gaps identified from patient data available in transactional systems of record. The methods can include creating a repository of educational material, measuring patient and team level performance gaps, associating the identified performance gaps with appropriate educational material, alerting the person about the appropriate educational material, capturing a user's interaction with the educational materials, and issuing credits or rewards for substantial consumption of the educational materials.

20 Claims, 8 Drawing Sheets

(56) References Cited

U.S. PATENT DOCUMENTS

| | | | | |
|---|---|---|---|---|
| 2008/0059292 | A1* | 3/2008 | Myers | G06Q 50/10 705/7.39 |
| 2008/0281639 | A1* | 11/2008 | Quinn | G06Q 10/10 705/3 |
| 2010/0266998 | A1* | 10/2010 | Tashiro | G09B 23/28 434/262 |
| 2011/0178813 | A1* | 7/2011 | Moore | G16H 10/60 705/2 |
| 2014/0186817 | A1* | 7/2014 | Wang | G09B 7/00 434/362 |
| 2014/0220543 | A1* | 8/2014 | Dohring | G09B 19/06 434/362 |
| 2014/0324457 | A1* | 10/2014 | Kim | G16H 10/60 705/3 |
| 2015/0161535 | A1* | 6/2015 | Ptashek | G06Q 10/06 705/2 |
| 2016/0019666 | A1* | 1/2016 | Amarasingham | G16H 40/20 705/3 |
| 2016/0042135 | A1* | 2/2016 | Hogan | G16H 50/20 705/2 |
| 2016/0196389 | A1* | 7/2016 | Moturu | G16H 50/20 705/2 |
| 2016/0358116 | A1* | 12/2016 | Cline | G06Q 10/063114 |
| 2017/0169715 | A1* | 6/2017 | Alyuz Civitci | G06N 20/10 |
| 2017/0286622 | A1* | 10/2017 | Cox | G06N 20/00 |
| 2018/0122509 | A1* | 5/2018 | Christiansson | G16H 10/60 |
| 2018/0247549 | A1* | 8/2018 | Martin | G06N 3/084 |
| 2019/0065597 | A1* | 2/2019 | Murray | G06N 5/022 |
| 2019/0213302 | A1* | 7/2019 | Abdolahi | G16B 45/00 |
| 2020/0111044 | A1* | 4/2020 | New, Jr | G06Q 10/063112 |
| 2020/0258622 | A1* | 8/2020 | Janssen | G16H 40/63 |
| 2021/0256615 | A1* | 8/2021 | Hayward | G06N 3/08 |

OTHER PUBLICATIONS

Moggizx, "mySQL—Triggers with complex configurable conditions", Stack Overflow, all pages, https://stackoverflow.com/questions/22167257/triggers-with-complex-configurable-conditions (Year: 2014).*

S.B. Kotsiantis, "Supervised Machine Learning: A Review of Classification Techniques", Jul. 16, 2007, Informatica 31 (2007) 249-268, all pages. (Year: 2007).*

L. C. Rabelo, A. Jones and Y. Yih, "Development of a real-time learning scheduler using reinforcement learning concepts," Proceedings of 1994 9th IEEE International Symposium on Intelligent Control, Columbus, OH, USA, 1994, pp. 291-296, doi: 10.1109/ISIC. 1994.367802. (Year: 1994).*

* cited by examiner

METHOD FOR RECOMMENDING CONTINUING EDUCATION TO HEALTH PROFESSIONALS BASED ON PATIENT OUTCOMES

STATEMENT REGARDING FEDERALLY SPONSORED RESEARCH

This invention was made with government support under Small Business Innovation Research Program awarded by the National Science Foundation. The government has certain rights in the invention.

BACKGROUND OF THE INVENTION

1. Field of the Invention

Embodiments of the invention relates generally to education methods. More particularly, the invention relates to methods for providing continuing education and nudges to health professionals, where the education modules may be based on patient outcomes.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

All health professionals are required to take continued education credits throughout their career in order to maintain their licenses and credentials current. This process was originally designed to be separate from the workplace setting. However, the speed of innovation in health care and competitive pressures on health care institutions require that training and education for health professionals be aligned to achieve results in patient outcomes. Learning management systems are the current technological solution used to deploy training and educational content to health professionals in workplace settings. However, these software systems have been unable to establish the relationships between a piece of training (or educational content/nudge) with any improvements in clinical outcomes.

Until now, the computer functionality to draw data from a database with patient information (like that found in Electronic Health Records and patient reported outcomes) and connect it with learning management systems to enable computations that train machine learning models to adjust individual patient health risk factor scores, assign patients to workflows and recommend personalized educational content was previously unavailable.

In view of the foregoing, there is a need for education methods that address the shortcomings of conventional methods.

SUMMARY OF THE INVENTION

Embodiments of the present invention are drawn to an automatic mechanism for providing health care professionals with personalized continued education content and nudges which address the skills necessary to improve the clinical outcomes of their specific patient populations.

This learning management system can include a computational engine capable of the following features. (1) Generating patient health risk factor scores or mathematical representations of individual level clinical and non-clinical factors through a machine learning model to predict potential adverse health episodes; (2) Assigning patients according to their health risk factor score to workflows using machine learning models that are trained to improve assignment logic and rules according to their effectiveness for achieving patient outcomes; (3) Storing and coding libraries of continued educational content by patient health risks, workflow components and learner preferences; (4) Identifying individual learner interests, learning styles and preferences by recording and sorting through their experiences engaging with the learning management system; (5) Recommending individualized continued education content to health professionals that addresses skills related to the health risks of their specific patient population, compliance with recommended workflows, learning styles and preferences; (6) Training machine learning models to identify which continued education content is correlated with improved patient outcomes and under what conditions; and (7) Presenting, capturing and reporting information related to the consumption of educational content which can be used to grant professionals with continued education credits.

The primary objective of SMART Patient-Centered Medical Home Manager (PCMH Manager) is to reduce and manage chronic disease by enabling team-based care in primary care practices. Embodiments of the present invention propose to apply precision-education instructional theory around team competencies to promote situational awareness, enhanced communication, defined role clarity, improved coordination and leadership support to improve patient outcomes. Various methods, according to embodiments of the present invention, include a web-based software that collects clinical and socioeconomic patient-level data and use machine learning to establish patient-specific risk scores to predict adverse health episodes. The software evaluates the effectiveness of team-level workflows and provides health professionals with individualized treatment plans and continued education to enhance patient outcomes.

According to one method of the present invention, the health care knowledge is suggested based on the performance health care provider or the care team(s) to which the health care provider is assigned. The method provides for creating or loading granules of health care knowledge and associating continuing education credits or other rewards with consuming the health care knowledge. Health care knowledge suggestions can be triggered for the health care professional based on measures calculated from patient demographic, clinical, and non-clinical data extracted from systems used by the health care provider and the care team(s) to which the health care provider is assigned. The measures calculated from patient demographic, clinical, and non-clinical data are compared to threshold values to decide whether to trigger a suggestion for a particular health care knowledge granule that are associated with information, skills, and aptitudes that are intended to improve the health care provider's performance. Therefore, the granules can be created so that they can be easily consumed in a short time period and have the potential for impacting patient care.

Methods of the present invention can be applied in a variety of contexts. The thresholds to which the measures calculated from patient demographic and clinical data can be set by a provider organization based on established care standards. If the provider is organization is seeking to increase performance level of a particular health care provider and the care team(s) to which the health care provider is assigned, it can choose to select thresholds that are based on statistical comparisons against the performance of other care teams in its facilities. This can be extended so that provider organizations can choose to select thresholds that are based on statistical comparisons against the performance of all care teams that are using a similar computer-assisted method.

In one method of the present invention, the health care knowledge associated with the triggered suggestion can be delivered immediately when the suggestion is generated so that the health care provider consumes it at that time. In the alternative, the alerts resulting from content suggestion triggers can be queued up so that the health care provider can respond to them whenever he or she has the opportunity to decide when to consume the suggested content. The information on how the health care professionals responds to the alerts in terms of timing, the content selected by the health care provider when offered similar options, and other characteristics of the process of responding to the alerts can be captured, synthesized, stored and later used to make predictions of how the alerts and the content can be delivered to maximize engagement and effectiveness. This would be a case of delivering health care content based on the health care provider's implied preferences rather than the specific preferences the health care provider may have established in his or her user profile.

Embodiment of the present invention can use data science techniques to identify the content consumption patterns of health care providers and care team(s) whose clinical performance has improved, specifically whenever causality between the content consumption and the clinical performance can be established and incorporate the associated content consumption model into the content suggestion trigger determination. As more data is available related to the use of this computer-assisted method, the manner in which the content suggestions are triggered can be transitioned from just comparison against clinical measure thresholds to a method that incorporates successful content consumption patterns, as well as the clinical measures, associated with the health care provider and the care team(s) to which the health care provider is assigned.

Embodiments of the present invention provide a method for providing continuing education a health care professional comprising continually assessing actual clinical performance of the health care professional as recorded in a clinical data system; creating a set of granules of health care knowledge or similar content in a database; associating continuing education credits with each granule of health care knowledge of the set of granules of health care knowledge; defining a set of configurable conditions that use data from the clinical data system to trigger appropriate granule suggestions to the health care provider; electronically delivering the appropriate health care knowledge granule based on the established preferences of the health care provider; recording the health care provider's interaction with the health care knowledge granule; determining whether the interaction with the health care knowledge granule is indicative that the health care provider consumed the health care knowledge granule; and recording continuing education credits based on the delivered health care knowledge granule if there is indication that the health care provider consumed the health care knowledge granule.

Embodiments of the present invention further provide a computer-assisted method for delivering health care knowledge to a health care provider, based on actual clinical performance recorded in a clinical data system comprising participating in interactions with patients and recording associated data in the clinical data system; acquiring relevant patient clinical data from the clinical data system; triggering one or more suggested health care knowledge granules based on performance of the health care provider; obtaining a request from the health care provider to deliver the suggested health care knowledge granules; delivering the suggested granules that were requested by the health care provider; recording an interaction of the health care provider with the health care knowledge granule; determining whether the interaction between the health care provider and health care knowledge granule was substantive; and recording continuing education credits based on the delivered health care knowledge granule if there is indication that the health care provider had a substantive interaction with the health care knowledge granule.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
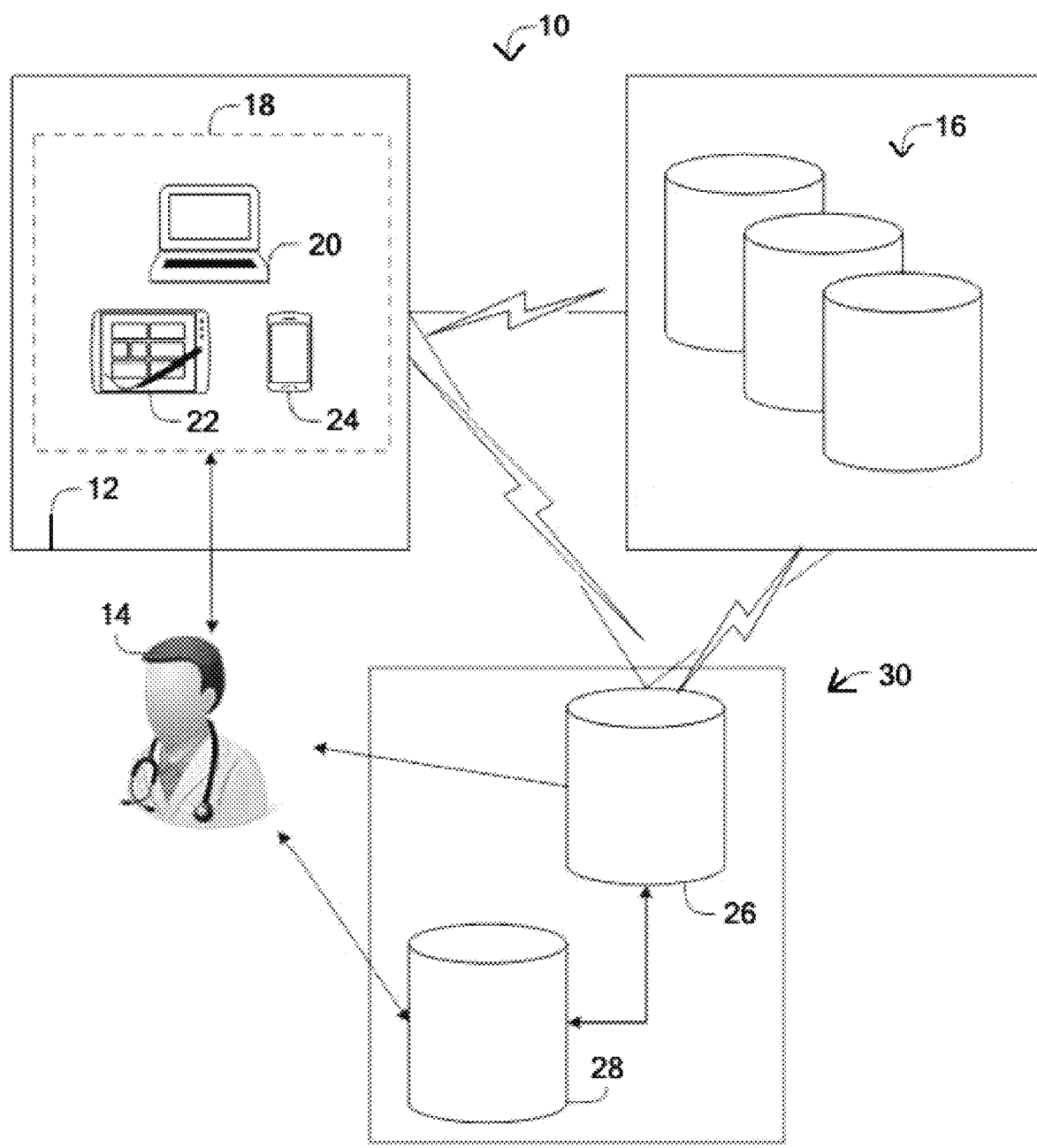
FIG. 1 illustrates a diagram showing one embodiment of the methodology of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary, a variety of optional components are described to illustrate the wide variety of possible embodiments of the present invention.

A "computer" or "computing device" may refer to one or more apparatus and/or one or more systems that are capable of accepting a structured input, processing the structured input according to prescribed rules, and producing results of the processing as output. Examples of a computer or computing device may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

"Software" or "application" may refer to prescribed rules to operate a computer. Examples of software or applications may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java.™., Jini.™., C, C++, Smalltalk, Python, Perl, UNIX Shell, Visual Basic or Visual Basic Script, Virtual Reality Markup Language (VRML), ColdFusion.™. or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). The program code may also be distributed among a plurality of computational units wherein each unit processes a portion of the total computation.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASHEEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G and the like.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory or may be communicated to an external device so as to cause physical changes or actuation of the external device.

Broadly, embodiments of the present invention provide methods and systems for providing health professionals with continued education based on performance gaps identified from patient data available in transactional systems of record. The invention can include creating a repository of educational material, measuring patient and team level performance gaps, associating the identified performance gaps with appropriate educational material, alerting the person about the appropriate educational material, capturing a user's interaction with the educational materials, and issuing credits or rewards for substantial consumption of the educational materials.

FIG. 1 illustrates the methodology of a system 10 according to an embodiment of the present invention. A point of care 12 is shown. The point of care 12 is a point at any time where the health care provider 14 meets the patient for a consultation or other interaction occurs between the health care provider 14 and a patient that impacts the patient health record in an electronic health record (EHR) or other clinical data systems 16. The health care provider 14 can utilize a number of devices 18 at the point of care 12 to connect to EHRs and other clinical data systems 16 to access patient data that can support the consultation or interaction. In addition, the health care provider 14 may enter information regarding the current consultation or interaction into the EHR of other clinical data systems 16. This can occur through a desktop or laptop computer 20, a tablet or similar computing device 22, or through a cellular phone 24 that is connected to the health care provider organization's internal network.

The information in the EHRs and other clinical data systems 16 may be uploaded by the patient information database 26 of the system through a variety of technical processes. The patient information database 26 can analyze the performance of the healthcare provider 14 or the care team(s) to which he or she is assigned to determine whether it falls within defined thresholds. If it does not, the patient information database 24 can display a message or send an alert to the healthcare provider 14 requesting that the healthcare provider read, view, or consume one or more specifically suggested health care knowledge granules that are available in the learning management computational engine 28.

The specified health care knowledge granules may relate directly to the thresholds that the healthcare provider and the care team(s) to which he or she is assigned did not meet. The relationship between the health care knowledge granules and the specific thresholds has been previously established by the system administrator or other user to whom such privileges have been assigned.

The health care provider 14 may receive the alert through pre-defined communications channels, which can include the system 30 or a message through other means, such as an SMS message. The healthcare provider 14 may elect to read, view, or consume the suggested health care knowledge granules immediately or wait until he or she deems it appropriate to do so. At such a time, the healthcare provider 14 may access the specific health care knowledge granules in the learning management computational engine 28. The interaction between the health care provider 14 and each healthcare knowledge granule may be captured by learning management computational engine 28, including whether the content was played in its entirety in the case of multimedia granules, the amount of time the health care provider interacted with the content, and any other parameter deemed to be relevant to determine whether the healthcare provider 28 substantially consumed the healthcare knowledge granule.

The learning management computational engine 28 can evaluate the captured parameters related to the interaction between the healthcare provider 28 and the granule against pre-specified thresholds. If the parameters captured as a result of the health care provider 14 interactions meet the specific criteria associated with the particular healthcare knowledge granule, as previously established by the system's administrator, the continuing education credits, recognition or other rewards associated with the healthcare knowledge granule can be issued in favor of the health care provider 14. The information regarding healthcare provider 14 continuing education credits or rewards may be stored in the patient information database 26 under the profile associated with the health care provider 14 and can be used as an input towards future decisions as to whether suggest the same healthcare knowledge granule or different ones whenever the performance of the healthcare provider 14 and the care team(s) to which he or she is assigned is once again analyzed or reviewed.

The method to select the content that is to be presented to the health care provider 14 can be implemented in a number of ways that take into consideration the performance of the health care provider 14 based on the information in the EHRs and other clinical data systems 16. The clinical standards and thresholds against which performance is evaluated may be defined and configured in the patient information database 26.

The present invention is not limited to any particular network topology or deployment model. In particular, the present invention can be implemented locally at the health care provider organization or at a different site. In the latter case, the system implementation site and the health care provider organization facility can be connected via a private network or through the Internet. The most significant advantages of using the Internet relate to (1) the ability to maintain a single learning management or content database that can be kept updated in a reliable manner so that knowledge granules may be accessed without concern as to quality or whether it is accredited. and (2) the ability to access content ubiquitously, i.e., without the need to be connected to the health care organization provider network.

Figure 2:
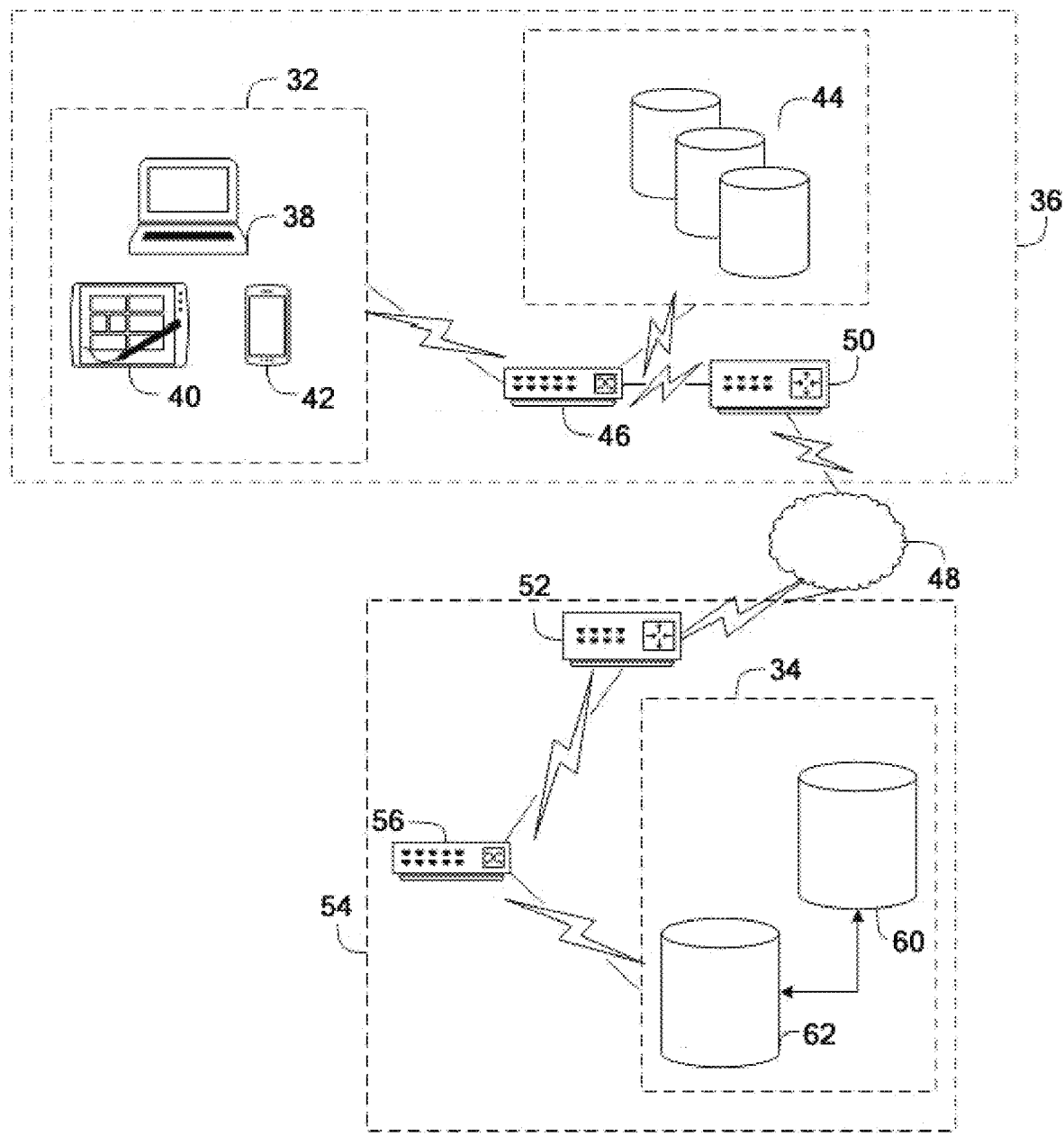
FIG. 2 illustrates a block diagram showing one implementation of a system according to the present invention in a use case associated with the use of an organization's internal network to access the system.

FIG. 2 shows a block diagram showing one implementation of a system according to the present invention in a use case associated with the use of an organization's internal network to access the system via the Internet. In the diagram, the client devices 32 that will access the system 34 may be deployed within the health care provider organization 36. The system 34 can be accessed occur through a desktop or laptop computer 38, a tablet or similar computing device 40, or through a cellular phone 42 that is connected to the health care provider organization's internal network. This can be accomplished through a wired or wireless connection in the health care provider organization 36 communications network. The health care provider organization's EHR system 44 may be connected to the same internal communications network. The client devices 32 do not need to be connected to the EHR system 44 via a network switch 46 in order to access the system 34. However, if the health care provider organization's EHR system 44 is not connected to the internal network and therefore cannot be accessed, the system 34 will not be able to upload patient data that has been captured in the health care provider organization's EHR system 44 since the last time in system uploaded data from the health care provider organization's EHR system 44. In order to connect to the system 34 via the Internet 48, the health care provider organization 36 may use an Internet router 50. The Internet router 50 can connect to its counterpart Internet router 52 in the site where the system 34 is implemented—"the system implementation site" 54. In order to communicate with the system 34, the Internet router 52 at the system implementation site 54 may be connected through a network switch 56. This scenario reflects a block diagram for the case discussed in FIG. 1, where client devices 32 can access the system 34 patient information database 60 and the learning management computational engine 62.

Figure 3:
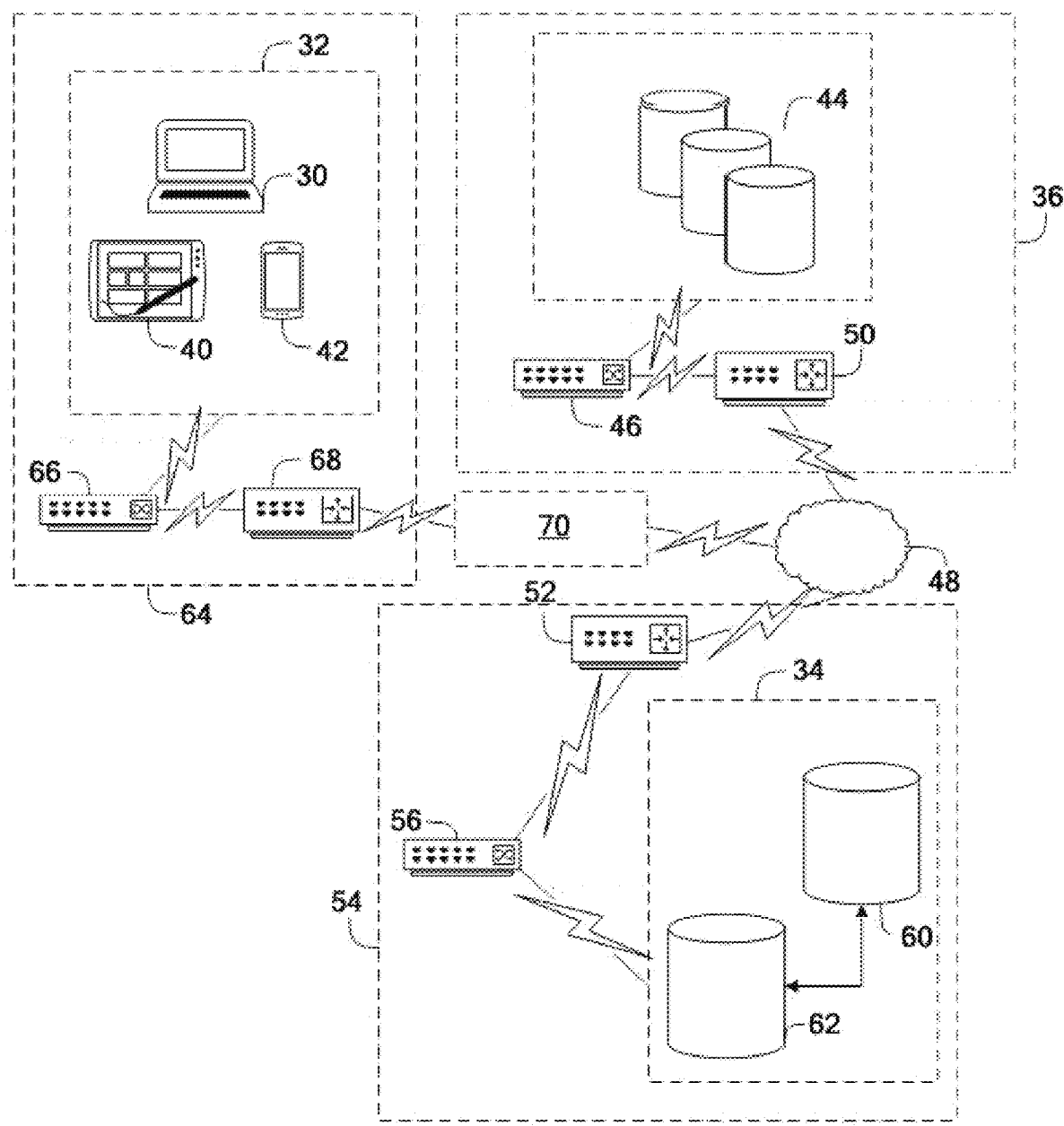
FIG. 3 illustrates a block diagram showing one implementation of a system according to the present invention in a use case associated with the use of a user's Internet Service Provider (ISP) to access the system.

In an implementation of the system where the implementation site is accessed via the Internet by the health care provider organization, there is the possibility of accessing the system from any device connected to the Internet via any ISP. This allows a health care provider to access the learning management computational engine at any time to consume the knowledge granules that have been suggested by the system. This use case is described in the block diagram of FIG. 3, which is a variation of the block diagram of FIG. 2. In this use case, the health care provider is in a location outside the health care provider organization facility and is not connected to the latter's internal network. Therefore, the health care provider is in a location where Internet access is controlled by a third-party, which could be an ISP. In FIG. 3, the client devices 32 that will access the system 34 are in a physical location outside the health care provider organization 36 and where there is no access to the latter's internal network. In this case, the user would connect the client device 32 to the Internet 48 through an internal network where a network switch 66 may connect the client device 32 to an Internet router 68. The Internet connection can be controlled by a third party, such as an ISP 70. The health care provider can then connect to the system 34, through the Internet router 52 at the system implementation site 54 which needs to be connected through a network switch 56. This use case is different from the one described in FIG. 1 in that the health care provider is not accessing the system at the point of care, but rather is a location outside the health care provider organization.

Figure 4:
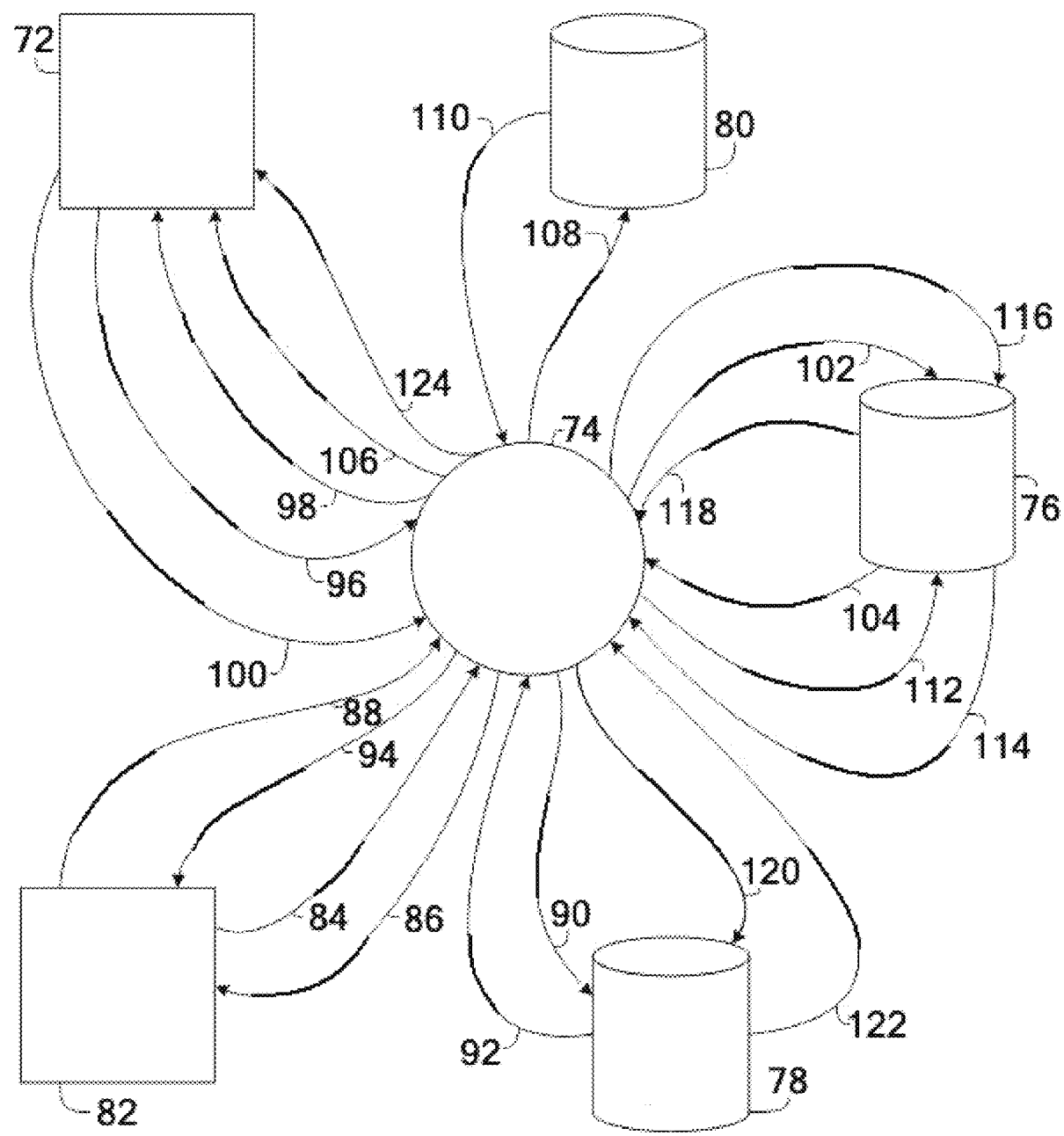
FIG. 4 provides a point of care work context diagram according to one embodiment of the present invention.

FIG. 4 provides a work context diagram for providing continuing medical education to a health care provider based on his or her actual clinical performance recorded in an EHR or similar clinical data system. In FIG. 4, a health care provider 72 or other members of the care teams to which a health care provider 72 is assigned can access a system application server 74, which orchestrates the system components: the patient information database 76 and the learning management computational engine 78. The system application server 74 may also controls communications with the health care provider organization's EHR database 80. Embodiments of the invention provides that there may be a designated content administrator 82 who is responsible for uploading, modifying, or managing content (knowledge granules) in the learning management computational engine 78 and providing the necessary metadata so that the system application server 74 can identify the knowledge granule alternatives associated with the performance gaps for the health care provider 72.

The system application server 74 can be implemented so that it makes decisions regarding the order in which it presents knowledge granules alternatives based on the explicit or implicit preferences of the health care provider 72. The explicit preferences are those that the health care provider 72 has explicitly selected as part of his or her profile in the patient information database 76, while the explicit preferences are those derived from the context in which the health care provider 72 has consumed suggested knowledge granules in the past. Embodiments of the invention can further provide that the content administrator 82 may be required to first make a login request 84 to the system application server 74, to which the application server can respond 86. The content administrator 82 could be in practically any physical location when making the login request 84 to the system application server 74. The content administrator 82 can be at the health care provider organization and connected to its internal network as in FIG. 2 or in any other physical location where a client device can connect to the Internet, as in FIG. 3. The content administrator 82 may be a third-party content provider, a representative of a medical credentialing organization, or any other person designated to manage the knowledge granules in the learning management computational engine 78. The only requirement for the content administrator 82 to make a login request 84 is that the client device being used by the content administrator 82 is connected to the system application server. In the scenarios and use cases in FIG. 2 and FIG. 3, this implies having internet connectivity. If the login response 86 is successful, the content administrator 82 can make a request to add, modify or manage content 88 to the system application server 74. In order to provide a response to the request 88, the system application server 74 would connect to the learning management computational engine 78 and relay the request 90. The learning management computational engine may respond 92 to the system application server's request 90 by confirming that the latter was completed. The system application server may then respond 94 to the content administrator's request to add, modify, or manage content 88. The content administrator's activities can ensure that the learning management computational engine 78 has the required knowledge granules to suggest content to the health care provider 72.

Embodiments of the invention can provide that the health care provider 72, whether at the point of care or elsewhere, may be required to first make a login request 96 to the system application server 74, to which the application server can respond 98. The health care provider 72 may want to add or modify data in the system related to his profile and content delivery preferences. This can be accomplished by submitting a request to add or modify data 100 to the system application server 74, which may generate the appropriate request 102 to the patient information database 76. Once the request is completed, the patient information database 76 may respond 104 to the system application server 74 request 102, which may be communicated back 106 to the health care provider 72.

One aspect of the present invention is the evaluation of health care provider performance against a set of thresholds or standards to determine if there are any gaps and making continuing medical education recommendations specifically focused on developing the knowledge and skills needed to bridge the identified gaps. In FIG. 4, there is no specific action that needs to be taken by the health care provider 72 to evaluate performance. This can be implemented in a number of ways, including a periodic evaluation of provider performance at a fixed time interval (e.g. monthly or quarterly), evaluating performance at a particular point in the care plan stored in the patient information database 76 for each patient, or evaluating provider performance after each encounter at the point of care. In the latter case, rules can be defined in the patient information database 76 to avoid notification fatigue. In addition, the appropriate interface may be implemented between the system application server 74 and the health care provider organization EHR database 80 to identify when a patient encounter has occurred.

Therefore, the system application server 74 may commence the health care provider 72 performance review whenever it is triggered by the established business rules.

The first step is to ensure that the patient information database 76 has updated information with regards to the performance of the health care provider 72. Thus, the system application server 74 may initiate a request for patient data 108 associated with the health care provider 72 to the health care provider organization EHR database 80, which may be an external system. If the request 108 is successful, the provider organization's EHR database 80 may respond 110 with available patient data. The system application server may then initiate a request 112 to the patient information database to add or modify data associated with a health care provider 72 and his or her patients. If successful, the patient information database 76 may respond 114 confirming that the requested addition or modification of data 112 was successful.

The system application server may request the necessary health care provider 72 performance data from the patient information database 116. Once the system application server 74 receives the response 118 from the patient information database 76, it may initiate a request 120 to the learning management computational engine 78 to identify the available knowledge granules that are associated with the specific health care provider 72 performance gaps identified in the patient information database 76. The learning management computational engine 78 may respond 122 with the links to the appropriate content.

As previously discussed, system application server 74 can be implemented so that it makes decisions regarding the order in which it presents knowledge granules alternatives based on the explicit or implicit preferences of the health care provider 72. The explicit preferences may be those that the health care provider 72 has explicitly selected as part of his profile in the patient information database 76, while the explicit preferences may be those derived from the context in which the health care provider 72 has consumed suggested knowledge granules in the past. The use of health care provider preferences would require that the information be included in the system application server request 116 to the patient information database 76 as well as the request 120 to the learning management computational engine 78 to obtain the implicit preferences. The information on the appropriate content (knowledge granules) may be presented to the health care provider 72 in the form of an asynchronous alert 124.

Figure 5:
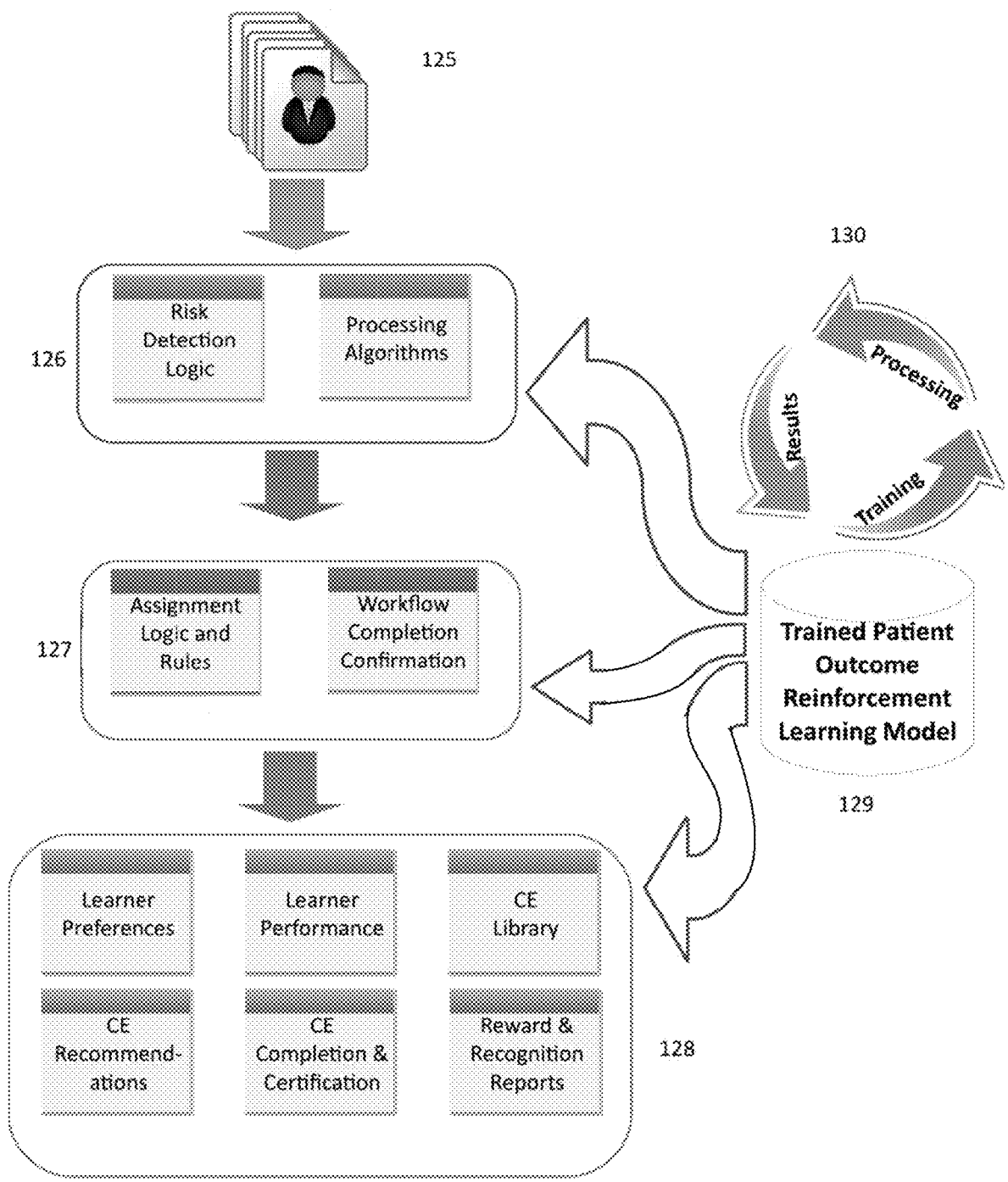
FIG. 5 provides a work context diagram for the computational engine, which can absorb data associated with patient risks and feed that to the patient risk factor machine learning system according to an embodiment of the present invention.

FIG. 5 provides a work context diagram for the computational engine, which can absorb data associated with patient risks 125 and feed that to the patient risk factor machine learning system 126. The patient risk factor machine learning system may process the using risk detection logic and other processing algorithms. This data may flow down to the patient workflow assignment system 127 where assignment logic and rules may be executed. The system 127 may also monitor for workflow tasks completion. From here, the Continuous Education (CE) deployment system 128 can absorb the information from the patient workflow assignment system 127 to provide users with recommended CE based on the preferences and previous performance, leveraging the CE library and promoting completion through the certifications and rewards and recognitions report. Each module may join with data from the train patient outcome reinforcement learning model 129 which may monitor results to identify required training and identify improvements in processes.

Figure 6:
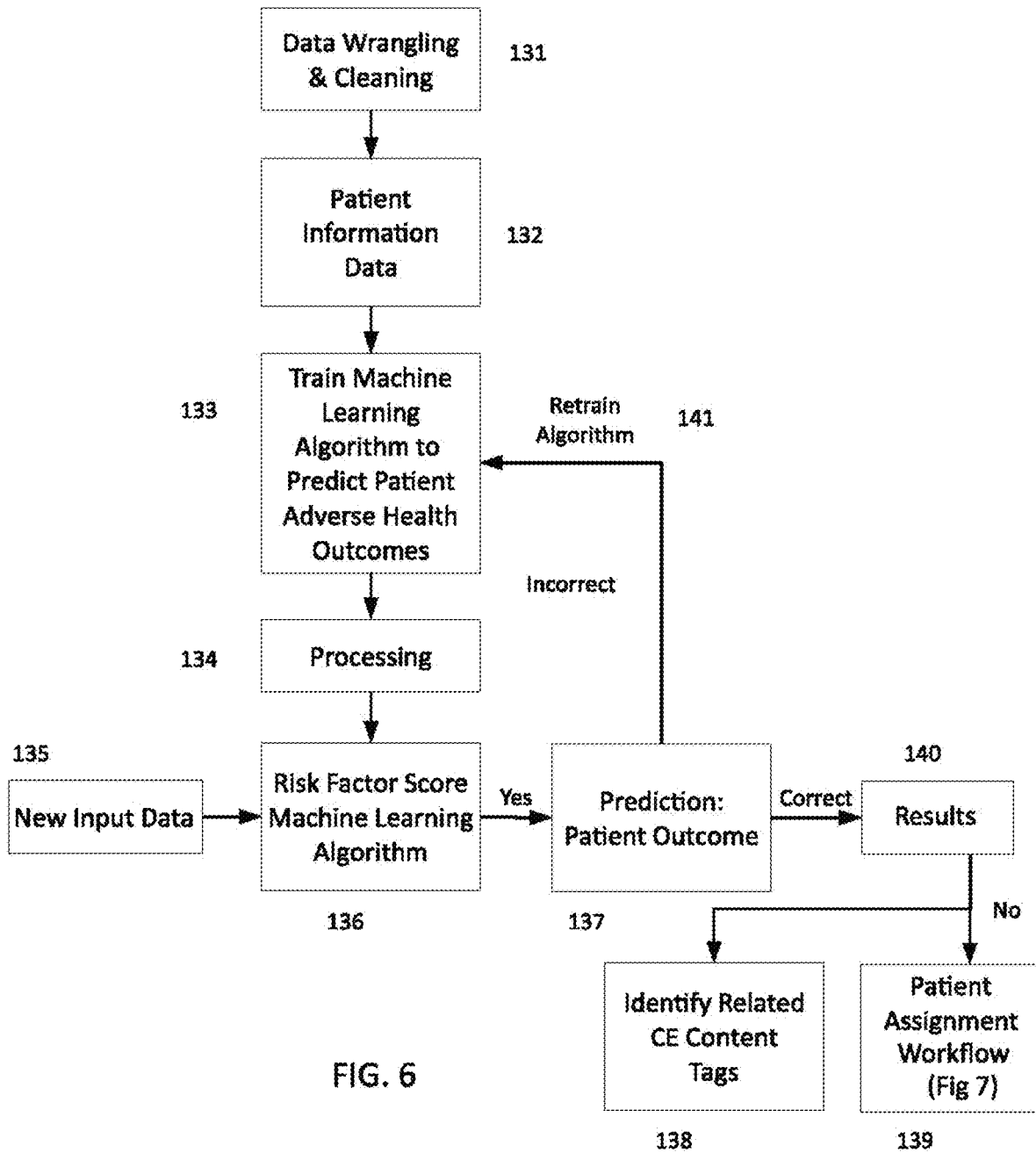
FIG. 6 provides additional details on the functionality of the patient risk factor machine learning system according to an embodiment of the present invention.

FIG. 6 provides additional details on the functionality of the patient risk factor machine learning system. This system may initiate a data clean-up process 131 which may prepare the patient information data 132 prior to the machine learning algorithm analyzing the data to predict patient adverse health outcomes using social determinants and clinical data 133. The results of the algorithm may be processed 134 and passed to the risk factor score machine learning algorithm 135, which may also receive new input data 136. This algorithm may identify if the predicted patient outcomes are correct per the patient results data 137. If the prediction is incorrect, the data may be fed back to the machine learning algorithm 133 to retrain the algorithm. If the prediction is correct, the results 140 may be used to identify related CE content tags 138 and the results 140 may be fed into the patient assignment workflow 139 in FIG. 7.

Figure 7:
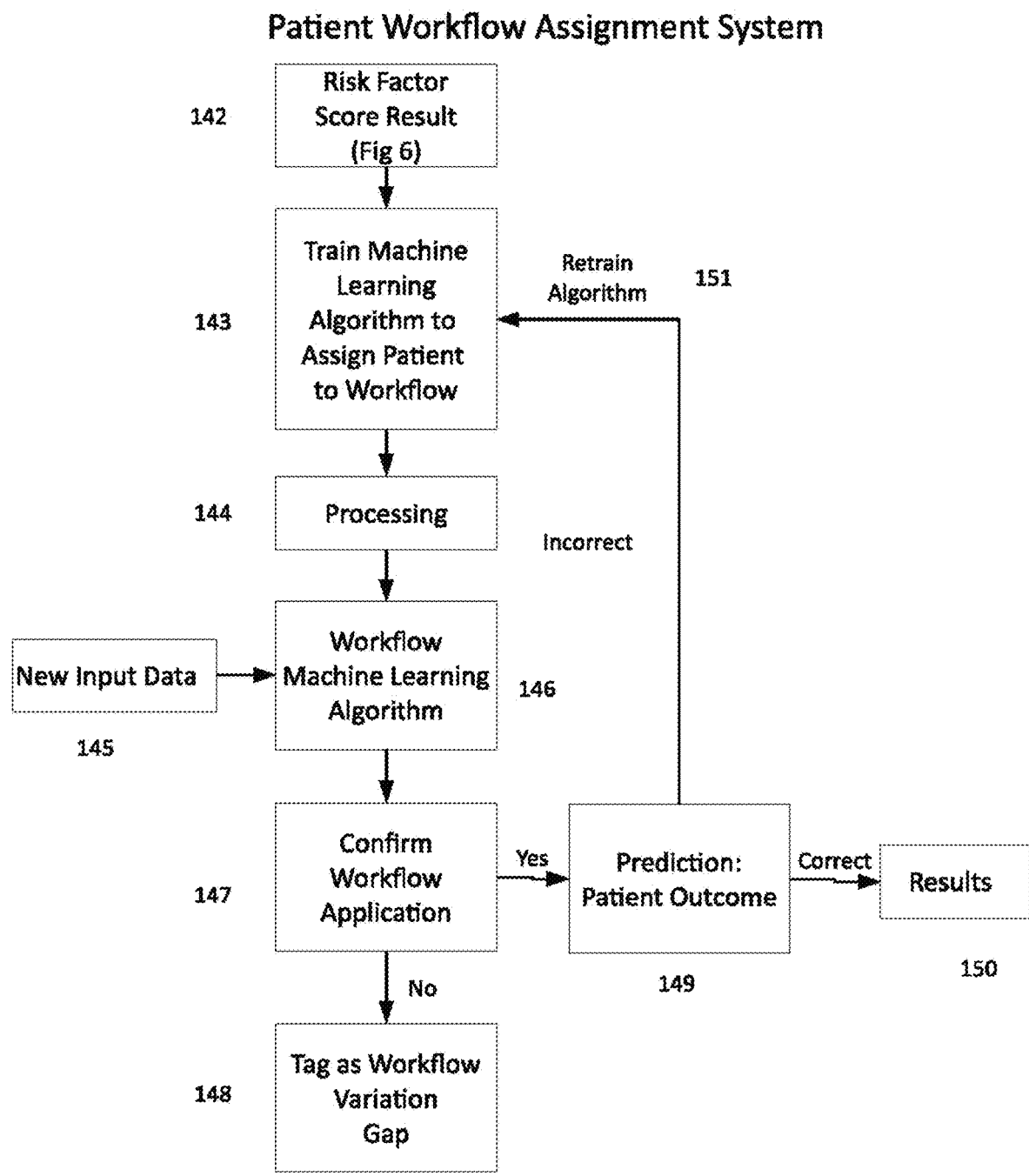
FIG. 7 provides additional details on the functionality of a patient workflow assignment system according to an embodiment of the present invention.

FIG. 7 provides additional details on the functionality of the patient workflow assignment system. Leveraging the results from the patient risk factor system 142, this system may train the machine learning algorithm on patient workflow assignments 143. This data may be processed 144, and the algorithm may provide workflow recommendations 146, taking in input data on workflow actions 145. This system may be monitoring user actions to confirm workflow application 147. If the workflow action was not executed, then it may tag the gap 148. If it was completed, then it may analyze the prediction for the patient outcomes 149. If the prediction is incorrect, the data may be fed back to the machine learning algorithm 151 to retrain the algorithm. If the prediction is correct, the results 150 may be stored and submitted to the CE deployment system in FIG. 8.

Figure 8:
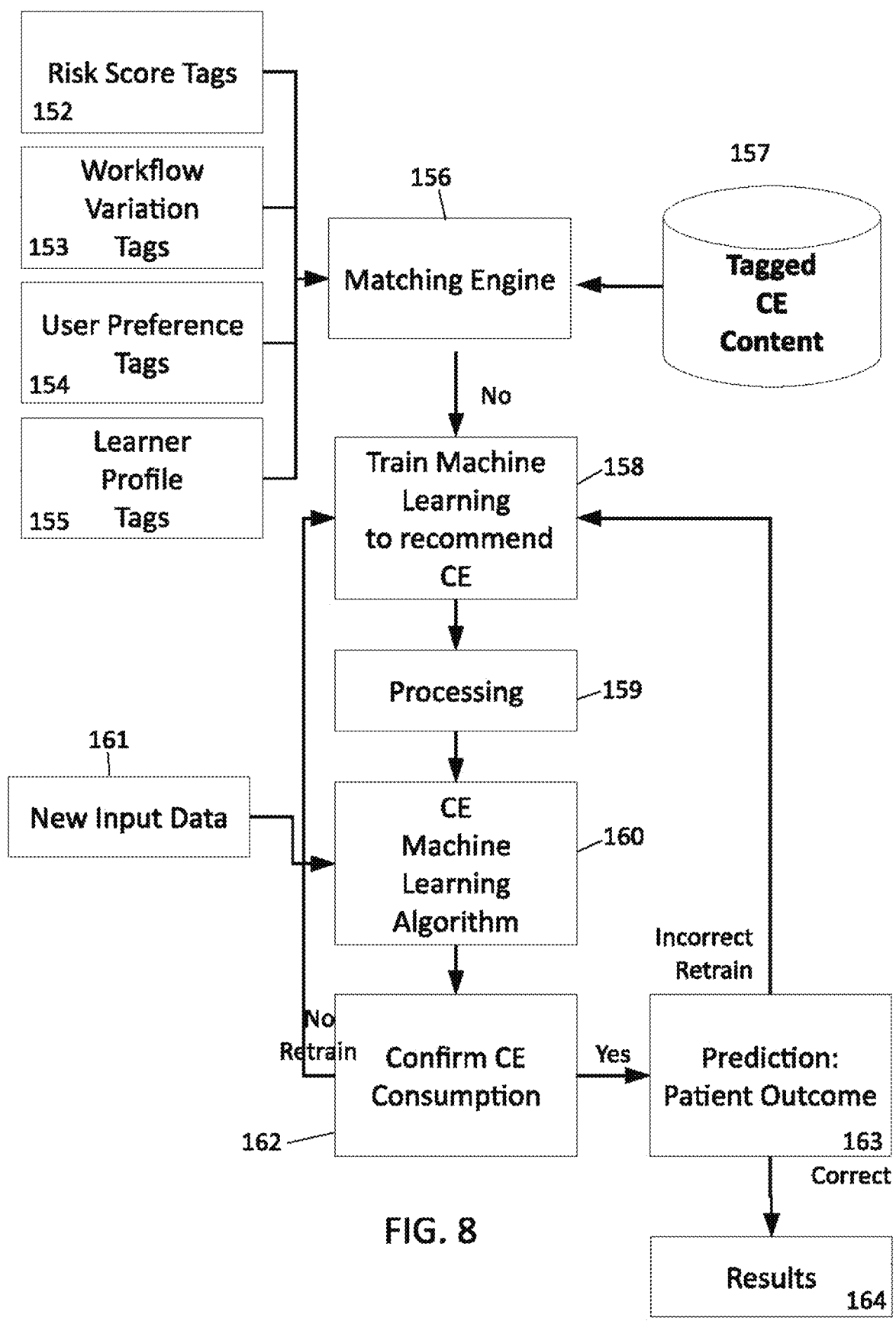
FIG. 8 provides a diagram of the continuous education deployment system according to an embodiment of the present invention.

FIG. 8 provides a diagram of the CE deployment system. This system may take in tagged CE content 157 from the patient risk factor machine learning system and risk score tags 152, workflow variation tags 153 from the patient workflow assignment system and user preference 154 and learner profile tags 155 stored in the system itself. The matching engine 156 may process this data and feed it to the machine learning algorithm to determine recommended CE 158. This data may be processed 159 and machine learning algorithm 159 may receive data from the system 161 to determine user actions align with the recommendations 162. If it determines that the CE was not consumed, it may feed the data back to the machine learning algorithm for retraining 158. If it was completed, then it may analyze the prediction for the patient outcomes 163. If the prediction is incorrect, the data may be fed back to the machine learning algorithm 158 to retrain the algorithm. If the prediction is correct, the results 164 may be stored.

Thus, a method for providing education suggestions based on actual performance has been disclosed. The present invention contemplates numerous variations in the type of information used, the topology of a network used to deliver the information, the type of devices used to access the information, the implementation model for the associated system, and other variations within the spirit and scope of the invention.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A method for providing continuing education to a health care professional comprising:
   continually assessing, electronically, via a system application server, actual clinical performance of the health care professional as recorded in a clinical data system;
   automatically creating a set of granules of health care knowledge in a database on the system application server, the set of granules of health care knowledge include information, skills, and aptitudes that are intended to improve performance of the health care provider;
   associating continuing education credits with each granule of health care knowledge of the set of granules of health care knowledge;
   analyzing the actual clinical performance of the healthcare provider continually to determine whether the actual clinical performance falls within defined thresholds;
   training patient health risk factor machine learning models to generate patient health risk factor scores using social determinants and clinical data that correlate workflow assignment to patient outcomes;
   training workflow assignment machine learning models to assign patients to workflows to achieve improved patient outcomes;
   using the workflow assignment machine learning models with the patient health risk factor scores to assign patients according to the patient health risk factor score to a workflow to improve assignment logic and rules for achieving patient outcomes;
   training continuing education machine learning models with data from the patient risk factor machine learning models, with workflow variation tags from the patient workflow assignment system, and with user preferences to identify which of the set of granules of health care knowledge is correlated with improved patient outcomes;
   defining a set of configurable conditions on the system application server that use data from the clinical data system to trigger granule suggestions to the health care provider;
   using the continuing education machine learning models to assess knowledge granules that are deployed in accordance with the learner's preferences and learning styles;
   electronically delivering the health care knowledge granule based on the established preferences of the health care provider automatically as triggered by clinical performance;
   recording the health care provider's interaction with the health care knowledge granule;
   determining whether the interaction with the health care knowledge granule is indicative that the health care provider consumed the health care knowledge granule; and
   recording continuing education credits based on the delivered health care knowledge granule if there is indication that the health care provider consumed the health care knowledge granule.

2. The method of claim 1 wherein the clinical data system is an electronic health record (EHR).

3. The method of claim 1 wherein the education credits can be substituted for electronic badges or other form of reward and recognition.

4. The method of claim 1 wherein the configurable conditions include data from a specific one of the health care providers and data from one or more care teams to which the health care provider is assigned.

5. The method of claim 4 wherein the configurable conditions include comparisons of the health care provider or care team data against at least one of (1) established care standards, (2) the performance of other care teams within a provider organization, and (3) performance of other care teams that are outside the provider organization, independently of their performance against established care standards.

6. A computer-assisted method for delivering health care knowledge to a health care provider, based on actual clinical performance recorded in a clinical data system, comprising:
   participating in interactions with patients and recording associated data in the clinical data system in communication with a system application server;
   automatically triggering one or more suggested health care knowledge granules based on performance of the health care provider, the one or more suggested health care knowledge granules electronically stored in a database of the system application server;
   obtaining a request, by the system application server, from the health care provider to deliver the suggested health care knowledge granules;
   delivering, by the database of the system application server, the suggested granules that are triggered for and/or requested by the health care provider;

recording an interaction of the health care provider with the health care knowledge granule on the system application server;

determining, by the system application server, whether the interaction between the health care provider and health care knowledge granule was substantive;

training workflow assignment machine learning models to assign patients to workflows to achieve improved patient outcomes;

training patient health risk factor machine learning models to generate patient health risk factor scores using social determinants and clinical data that correlate workflow assignment to patient outcomes;

training continuing education machine learning models with data from the patient risk factor machine learning models, with workflow variation tags from the patient workflow assignment models, and with user preferences to identify which knowledge granules are correlated with improved patient outcomes and under what conditions;

using the continuing education machine learning models to assess knowledge granules that are related to the learner's preferences and learning styles;

using the workflow assignment machine learning models to assign patients according to the patient health risk factor score to a workflow to improve assignment logic and rules for achieving patient outcomes; and recording, on the system application server, continuing education credits based on the delivered health care knowledge granule if there is indication that the health care provider had a substantive interaction with the health care knowledge granule.

7. The method of claim 6 wherein the clinical data system is an electronic health record (EHR).

8. The method of claim 6, further comprising triggering one or more health care knowledge granule suggestions based on performance of the health care provider and one or more care teams to which the health care provider is assigned.

9. The method of claim 6, further comprising delivering a requested health care knowledge granule based on saved or inferred preferences of the health care provider using machine learning algorithms.

10. The method of claim 6 further comprising:
accessing at least one related granule of health care knowledge; and
documenting continuing education credits based on the at least one related granule of health care knowledge.

11. The method of claim 6 further comprising extracting clinical data from the clinical data system used by the health care provider to record a patient's demographic and clinical information, including at least one of problem lists, clinical procedures, diagnostic codes, ancillary service orders, and results of the ancillary service orders.

12. The method of claim 6 further comprising computing at least one of quality clinical measures, gaps in care, outcomes, and other objective measures for the health care provider.

13. The method of claim 6 further comprising comparing at least one of the health care provider's quality clinical measures, gaps in care, outcomes, and other objective measures against at least one of (1) established clinical care standards, (2) performance of other care teams within a provider organization, and (3) performance of other care teams that are outside the provider organization, independently of their performance against standards using reinforcement learning algorithms focused on improving patient outcomes.

14. The method of claim 6 further comprising triggering health care knowledge suggestions based on the results of at least one of a comparison of quality clinical measures, gaps in care, outcomes, and other objective measures for the health care provider.

15. The method of claim 14 further comprising saving the health care knowledge suggestions as alerts in a queue that the health care provider can respond to whenever it is convenient.

16. The method of claim 15 further comprising capturing a response to the alerts by the health care provider.

17. The method of claim 6 further comprising delivering the suggested health care knowledge granules that were approved for delivery by the health care provider in a manner, format, or method associated with saved or inferred preferences of the health care provider.

18. The method of claim 6 further comprising recording details of an interaction of the health care provider with the delivered health care knowledge granule.

19. The method of claim 18 further comprising using details of the health care provider's interaction to determine whether the health care provider's interaction with the health care knowledge granule was substantive or not.

20. The method of claim 19 further comprising issuing the continuing education credits in favor of the health care provider for any knowledge granule where the health care provider's interaction was substantive.

* * * * *